United States Patent
Wright et al.

(10) Patent No.: US 8,236,731 B2
(45) Date of Patent: Aug. 7, 2012

(54) HERBICIDE COMPATIBILITY IMPROVEMENT

(75) Inventors: Daniel R. Wright, St. Louis, MO (US); John W. Hemminghaus, Crestwood, MO (US); David R. Eaton, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1752 days.

(21) Appl. No.: 11/438,573

(22) Filed: May 22, 2006

(65) Prior Publication Data
US 2006/0270556 A1    Nov. 30, 2006

Related U.S. Application Data

(60) Provisional application No. 60/684,024, filed on May 24, 2005.

(51) Int. Cl.
*A01N 57/18* (2006.01)
(52) U.S. Cl. .................................................. 504/206
(58) Field of Classification Search .................. None
See application file for complete search history.

(56) References Cited

U.S. PATENT DOCUMENTS

| | | | |
|---|---|---|---|
| 5,652,197 A | 7/1997 | Claude et al. | 504/206 |
| 5,668,085 A | 9/1997 | Forbes et al. | 504/206 |
| 5,750,468 A | 5/1998 | Wright et al. | 504/206 |
| 6,455,473 B2 | 9/2002 | Wright | 504/206 |
| 6,544,930 B2 * | 4/2003 | Wright | 504/206 |
| 2003/0125209 A1 | 7/2003 | Tank | 504/206 |
| 2006/0040826 A1 | 2/2006 | Eaton et al. | 504/206 |

FOREIGN PATENT DOCUMENTS

| | | |
|---|---|---|
| WO | WO 99/21424 | 5/1999 |
| WO | WO 01/89302 | 11/2001 |
| WO | WO 03/013241 | * 2/2003 |
| WO | WO 02/34047 | 5/2005 |
| WO | WO 2005/087007 | 9/2005 |
| WO | WO2006/023431 | 3/2006 |

OTHER PUBLICATIONS

Roundup Weathermax Herbicide; http://www.monsanto.com/monsanto/us_ag/content/crop_pro/roundup_weathermax/label.pdf.
PCT International Search Report and Written Opinion for PCT/US2006/019543.

* cited by examiner

*Primary Examiner* — James H. Alstrum-Acevedo
*Assistant Examiner* — Daniel L Branson
(74) *Attorney, Agent, or Firm* — Joseph A. Schaper; Harness, Dickey & Pierce, P.L.C.

(57) ABSTRACT

A herbicidal composition comprises an aqueous solution of one to a plurality of salts of glyphosate at a total glyphosate a.e. concentration not less than about 360 g/l, wherein (a) said glyphosate is in anionic form accompanied by low molecular weight non-amphiphilic cations in a total molar amount of about 110% to about 120% of the molar amount of said glyphosate; and (b) a major amount to substantially all of the low molecular weight non-amphiphilic cations are potassium cations. The composition exhibits improved tank-mix compatibility with a phenoxy-type herbicide salt formulation by comparison with an otherwise similar composition having a lower molar amount of said low molecular weight non-amphiphilic cations.

21 Claims, No Drawings

HERBICIDE COMPATIBILITY IMPROVEMENT

This application claims the benefit of U.S. provisional patent application Ser. No. 60/684,024, filed on May 24, 2005, the entire disclosure of which is incorporated by reference herein.

FIELD OF THE INVENTION

The present invention relates to methods and compositions that improve compatibility of herbicides when mixed, for example in a spray tank. In particular, the invention relates to compatibility in a tank mixture of aqueous formulations of herbicides that are in the form of salts, more particularly where the mixture comprises salts of glyphosate and a phenoxy-type herbicide.

BACKGROUND OF THE INVENTION

Economics of distribution of agricultural chemicals, such as herbicides in general and glyphosate formulations in particular, can be much improved through provision of a high "loading" of active ingredient in the formulation, that is, the amount of active ingredient that can be accommodated in a container of given capacity.

Glyphosate is an acid that is relatively insoluble in water (1.16% by weight at 25° C.). For this reason it is typically formulated as a water-soluble salt in aqueous solution. A useful alternative is to prepare glyphosate as a dry salt in powder or granular form. For example, a dry water-soluble granular formulation of glyphosate ammonium salt can have a glyphosate acid equivalent (a.e.) content as high as about 86% by weight. This would appear at first sight to provide an excellent solution to the challenge of packing more glyphosate into a container of given capacity. Unfortunately the benefit of a dry glyphosate formulation in this regard is more limited than one might expect, because such a formulation tends to have low bulk density. Also, many end-users and many distributors prefer a liquid product because of flexibility in handling, thus a need remains for high-loaded liquid formulations of glyphosate.

U.S. Pat. No. 6,544,930 to Wright discloses an approach to meeting this challenge. According to this approach, a concentrated aqueous solution of glyphosate, predominantly in the form of one or a mixture of the potassium and monoethanolammonium (MEA) salts thereof, was provided, it having been determined that such a solution had an unexpectedly high specific gravity, permitting more glyphosate a.e. to be delivered in a container of given capacity than was previously attainable using the isopropylammonium (IPA) salt in widespread commercial use, for example as Roundup® herbicide of Monsanto.

Unfortunately, glyphosate potassium salt, especially when formulated at high concentration in aqueous solution, brings some challenges of its own. For example, where (as often) it is desired to coformulate a surfactant with the glyphosate, physical incompatibility of the surfactant with the glyphosate salt can limit the options available. Whereas a range of surfactants are compatible with glyphosate IPA salt, fewer have been found to be compatible with glyphosate potassium salt, in particular where the salt is present at high concentration. See above-cited U.S. Pat. No. 6,544,930, col. 9, lines 6-13.

Another challenge arises where a user of a glyphosate potassium salt formulation wishes to add to that formulation, with dilution in water (for example in a spray tank) a second herbicide that is also in a form of a salt, for example a phenoxy-type herbicide salt such as an organic ammonium, illustratively dimethylammonium (DMA) salt of 2,4-dichlorophenoxyacetic acid (2,4-D), to form a tank mixture. Such tank mixtures of glyphosate and phenoxy-type herbicides are widely used, but their use can be limited by a tendency, under certain conditions, for precipitation of solids that can settle and clog filters or nozzles of field spraying equipment. This tendency is evidence of physical incompatibility of the glyphosate salt and the phenoxy-type herbicide salt under such conditions.

International Patent Publication No. WO 03/013241 proposes, inter alia, a glyphosate composition comprising IPA and potassium cations in a mole ratio of 1:10 to 30:1, "more preferably less than 15:1 and greater than 1:2", reportedly as a means to improve bioefficacy over compositions of a single glyphosate salt.

U.S. Patent Application Publication No. 2003/0125209 states that viscosity of concentrated glyphosate IPA formulations can be reduced by using a lower molar excess of IPA than a 15-20% molar excess, said therein to be "typical". A glyphosate/IPA mole ratio "between about 1.00:1.00 and about 1:00:1.10 . . . , preferably between 1:00:1.00 and about 1.00:1.05" is proposed therein.

Publications cited above are incorporated herein by reference.

Considering the variety of conditions and special situations under which glyphosate herbicides are used around the world, there remains a need for aqueous concentrate formulations of glyphosate, including surfactant-containing formulations, providing benefits under at least some of those conditions and situations. There is an especial need for such formulations having high glyphosate loading, for example at least about 400 g a.e./l, that are compatible when tank mixed with phenoxy-type herbicide salts under a wide range of field conditions.

SUMMARY OF THE INVENTION

A "glyphosate potassium salt" formulation herein is a glyphosate salt formulation wherein a major amount to substantially all of the salt-forming cations are potassium cations. Other salt-forming cations, such as ammonium and organic ammonium cations, are optionally present in such a formulation to a minor degree, for example not more than about 50%, typically not more than about 30%, by molar amount of all salt-forming cations present.

It has now surprisingly been found that a small increase in the molar excess of cations in a glyphosate potassium salt formulation can result in improved tank-mix compatibility of such a formulation with a phenoxy-type herbicide salt. Too great an increase in the molar excess of cations can result in reduced surfactant compatibility, as evidenced by a lowering of cloud point to an unacceptable level; thus, where a surfactant is included in the glyphosate salt formulation, it is important not to exceed a maximum molar excess consistent with acceptable cloud point.

Even more surprisingly, it has now been found that where cations added to a glyphosate potassium salt formulation to achieve molar excess are organic ammonium (e.g., IPA) cations rather than potassium cations, tank-mix compatibility at equivalent molar excess can be further improved.

Accordingly, there is now provided a herbicidal composition comprising in aqueous solution one to a plurality of salts of glyphosate at a total glyphosate a.e. concentration not less than about 360 g/l, wherein (a) said glyphosate is in anionic form accompanied by low molecular weight non-amphiphilic cations in a total molar amount of about 110% to about 120% of the molar amount of said glyphosate; and (b) a major amount to substantially all of the low molecular weight non-amphiphilic cations are potassium cations. The composition exhibits improved tank-mix compatibility with a phenoxy-type herbicide salt formulation by comparison with an otherwise similar composition having a lower molar amount of said low molecular weight non-amphiphilic cations.

There is also provided a composition as just described, further comprising at least one surfactant, wherein the weight ratio of glyphosate (expressed as a.e.) to surfactant is not greater than about 10:1.

In an embodiment of the invention, the composition comprises a mixture of potassium and low molecular weight organic ammonium salts of glyphosate wherein the mole ratio of potassium to low molecular weight organic ammonium cations is about 55:45 to about 99:1.

In a further embodiment, the composition comprises glyphosate potassium salt having no more than a pH adjusting amount of low molecular weight organic ammonium cations. A "pH adjusting amount" in the present context means an amount sufficient to raise pH of a glyphosate potassium salt solution, as determined by a method substantially as taught herein, by up to about 0.5 pH unit.

A tank-mix herbicidal composition, prepared by admixing a glyphosate salt composition as provided above and a phenoxy-type herbicide salt in a glyphosate to phenoxy-type herbicide a.e. ratio of about 1:5 to about 20:1, is also an embodiment of the present invention. Accordingly, there is provided a tank-mix herbicidal composition comprising, in an aqueous application medium, a glyphosate herbicide and a phenoxy-type herbicide, the composition being prepared by a process comprising admixing in a suitable vessel with agitation:

(i) water in an amount suitable for application to a plant and/or soil surface by spraying;
(ii) a herbicidally effective amount of a first aqueous concentrate herbicidal composition comprising in aqueous solution one to a plurality of salts of glyphosate at a total glyphosate a.e. concentration not less than about 360 g/l, wherein (a) said glyphosate is in anionic form accompanied by low molecular weight non-amphiphilic cations in a total molar amount of about 110% to about 120% of the molar amount of said glyphosate; and (b) a major amount to substantially all of the low molecular weight non-amphiphilic cations are potassium cations; and
(iii) a second aqueous concentrate herbicidal composition comprising in aqueous solution one to a plurality of salts of the phenoxy-type herbicide, in an amount providing a glyphosate to phenoxy-type herbicide a.e. ratio of about 1:5 to about 20:1.

There is still further provided a process for preparing a tank-mix herbicidal composition, the process comprising admixing in a suitable vessel with agitation:

(i) water in an amount suitable for application to a plant and/or soil surface by spraying;
(ii) a herbicidally effective amount of a first aqueous concentrate herbicidal composition comprising in aqueous solution one to a plurality of salts of glyphosate at a total glyphosate a.e. concentration not less than about 360 g/l, wherein (a) the glyphosate is in anionic form accompanied by low molecular weight non-amphiphilic cations in a total molar amount of about 110% to about 120% of the molar amount of glyphosate; and (b) a major amount to substantially all of the low molecular weight non-amphiphilic cations are potassium cations; and
(iii) a second aqueous concentrate herbicidal composition comprising in aqueous solution one to a plurality of salts of the phenoxy-type herbicide, in an amount providing a glyphosate to phenoxy-type herbicide a.e. ratio of about 1:5 to about 20:1.

There is still further provided a method for improving compatibility of an aqueous concentrate glyphosate potassium salt composition with an aqueous concentrate phenoxy-type herbicide salt composition when admixed with water to form a tank-mix composition, the method comprising adding a base in an amount sufficient to raise pH of the tank-mix composition to at least about 4.8.

There is still further provided a method for redissolving a precipitate that forms when an aqueous concentrate glyphosate potassium salt composition and an aqueous concentrate phenoxy-type herbicide salt composition are admixed with water to form a tank-mix composition, the method comprising adding a base in an amount sufficient to redissolve the precipitate.

There is still further provided a process for preparing an aqueous concentrate glyphosate salt composition, the process comprising:

(i) neutralizing glyphosate acid with potassium hydroxide and optionally a minor amount of a low molecular weight organic amine in presence of water to produce a slurry or concentrated glyphosate salt solution having a pH of about 4.4 to about 4.7;
(ii) adding water if necessary and optionally at least one surfactant to produce a final composition having a total glyphosate a.e. concentration not less than about 360 g/l; and
(iii) adding a low molecular weight organic amine in an amount sufficient to provide a pH of about 4.8 to about 5.0 in the final composition;

wherein the low molecular weight organic amine is added before, during or after addition of the water to produce the final composition.

DETAILED DESCRIPTION

A herbicidal composition of one embodiment of the invention comprises in aqueous solution one to a plurality of salts of glyphosate at a total glyphosate a.e. concentration not less than about 360 g/l. The glyphosate is in anionic form accompanied by low molecular weight non-amphiphilic cations in a total molar amount of about 110% to about 120% of the molar amount of the glyphosate. A major amount to substantially all of the low molecular weight non-amphiphilic cations are potassium cations.

By "total glyphosate a.e. concentration" is meant the concentration of glyphosate in all forms present, expressed as acid equivalent. An upper limit for such concentration is dictated by the limit of solubility of the particular salt or mixture of salts present, but in absence of other ingredients such as a surfactant a total glyphosate a.e. concentration of up to about 650 g/l or even higher can be achieved in some instances. In presence of surfactant, a practical upper limit is typically about 600 to about 620 g/l.

In various embodiments the total glyphosate a.e. concentration in the composition is not less than about 400 g/l, not less than about 450 g/l, not less than about 480 g/l, or not less than about 540 g/l.

A "low molecular weight non-amphiphilic cation" herein is distinguished from higher molecular weight cationic entities that can be contributed by certain surfactants such as polyoxyethylene tertiary amines, etheramines and quaternary ammonium surfactants. It will be understood, therefore, that such higher molecular weight entities, even if present, are not to be included in any calculation of molar amount of cations for purposes of the invention. Low molecular weight non-amphiphilic cations illustratively include alkali metal cations such as potassium and sodium cations, ammonium cations, low molecular weight organic ammonium cations such as methylammonium, dimethylammonium, propylammonium (n-propylammonium and isopropylammonium), mono-, di- and triethanolammonium cations, and low molecular weight organic sulfonium cations such as trimethylsulfonium cations.

In the present compositions, at least a major amount (i.e., more than 50 mole %) of the low molecular weight non-amphiphilic cations are potassium cations. In various embodiments, at least about 55 mole %, at least about 60 mole %, at least about 65 mole %, at least about 70 mole %, at least about 75 mole %, at least about 80 mole %, at least about 85 mole % or at least about 90 mole % of the low molecular weight non-amphiphilic cations are potassium cations.

Where potassium cations constitute less than 100% of all low molecular weight non-amphiphilic cations present in the composition, the balance can be provided by any one or more such cations other than potassium, including without limitation those mentioned above. In one embodiment, the balance is provided in part or in whole by low molecular weight organic ammonium cations. In various embodiments a mole ratio of potassium to organic ammonium cations of about 55:45 to about 99:1, about 60:40 to about 99:1, about 70:30 to about 99:1, about 55:45 to about 95:5, about 60:40 to about 95:5, about 70:30 to about 95:5, about 55:45 to about 90:10, about 60:40 to about 90:10 or about 70:30 to about 90:10 is present.

In more specific embodiments, the organic ammonium cations if present comprise propylammonium cations. In even more specific embodiments, the organic ammonium cations if present comprise isopropylammonium (IPA) cations.

Optionally more than one species of low molecular weight organic ammonium cations can be present, in any suitable ratio.

In selecting a suitable mole ratio of potassium to organic ammonium cations, it may be helpful to note that at a mole ratio substantially lower than about 70:30, it becomes more difficult to provide a composition with high glyphosate loading as desired herein; and that at a mole ratio higher than about 90:10, surfactant compatibility, as measured for example by cloud point, can be reduced. It will be recognized that not all surfactants give rise to cloud point problems; glyphosate formulations with alkyl polyglucosides (APGs), for example, typically do not exhibit a cloud point.

In a composition comprising potassium and IPA cations, the mole ratio of potassium to IPA cations in various non-limiting embodiments is about 70:30 to about 90:10, about 75:25 to about 85:15 or about 77:23 to about 83:17, for example about 80:20. Illustratively, a suitable potassium/IPA mole ratio can be about 2.5:1 to about 7.5:1, i.e., about 71:29 to about 88:12, for example about 3:1 to about 6:1, i.e., about 75:25 to about 86:14).

The low molecular weight non-amphiphilic cations in total constitute about 110% to about 120% of the molar amount of the glyphosate in the composition. In other words, the composition has a "base excess" of about 10% to about 20%.

The pH of the composition is an indicator of the level of base excess. However, pH is difficult to measure to the degree of accuracy needed to precisely determine the level of base excess, and a measured pH value of a given composition can depend on the precise protocol followed in making the measurement. As guidance, however, a composition having a pH not lower than about 4.8, as determined by a procedure substantially as described below, will generally be found suitable. Illustratively, the pH can be about 4.8 to about 7.0, for example about 4.8 to about 6.0, about 4.8 to about 5.0, about 4.85 to about 4.99 or about 4.9 to about 4.98.

Measurement of pH can be according to any suitable protocol. For example, a sample of a test formulation of known weight is diluted in demineralized water to make a total solution mass of, say, 100 g, which is agitated, e.g., with a magnetic stirring bar. A pH meter capable of measuring pH to at least 2 decimal places, and fitted with an electrode with temperature compensation, is calibrated with standard buffers, for example at pH 4.0 and pH 7.0. The solution pH is recorded when a stable reading is obtained. Between sample measurements, the electrode should be washed with and stored temporarily in demineralized water. After all sample measurements, the calibration is rechecked against the standard buffers. Illustration of use of such a protocol is found in Example 9 hereinbelow.

Because of the vagaries of pH determination, it is possible that a composition having a level of base excess as recited herein has a measured pH slightly outside the ranges given above for guidance. In such a case, base excess or mole ratio as determined analytically or by stoichiometry from formulation records will be understood to be dispositive.

Commercial formulations based on glyphosate IPA salt commonly have a base excess of no more than about 5% to about 10%, and the active ingredient of such formulations is often referred to as "mono(isopropylammonium) glyphosate" to reflect a glyphosate/IPA mole ratio close to 1:1. Increasing the mole ratio of anions to cations substantially above 1:1.2 (i.e., providing a base excess substantially greater than 20%) not only adds unnecessary cost through the resulting excess of the cationic species used, but can reduce the upper limit of solubility of the salt mixture, especially in presence of surfactant. According to the present invention, a minimum of about 10% base excess is desirable to enhance tank-mix compatibility with phenoxy-type herbicide salts. Thus, for practice of the invention, the total molar amount of low molecular weight non-amphiphilic cations should be about 110% to about 120% of the molar amount of glyphosate. In various embodiments, the base excess can be about 12% to about 20%, about 15% to about 20%, about 12% to about 18% or about 15% to about 18%.

In one embodiment, the composition is based predominantly on glyphosate potassium salt, but low molecular weight organic ammonium cations, for example propylammonium such as IPA cations, are present in no more than a pH adjusting amount as defined hereinabove. The amount of such organic ammonium cations can, in various embodiments, be sufficient to raise pH by about 0.1 to about 0.5 units, for example about 0.2 to about 0.5 units, in a pH range from about 4.4 to about 5.0. A molar ratio of potassium to low molecular weight organic ammonium cations of about 95:5 to about 99:1, for example about 96:4 to about 98:2, illustratively about 97:3, will generally be found suitable.

While a composition of the invention can consist essentially of nothing more than the above-described glyphosate salt or mixture of glyphosate salts in aqueous solution, advantages of the invention become particularly great when one or more surfactants are also included in the composition in an agronomically useful amount.

An "agronomically useful amount" means a sufficient amount of the surfactant or surfactants to provide a benefit in terms of improved herbicidal effectiveness by comparison with an otherwise similar glyphosate composition lacking surfactant. What constitutes an agronomically useful amount depends on the particular surfactant(s) selected, the plant species to be treated with the herbicidal composition, application spray volume, environmental and other factors. Typically a minimum agronomically useful amount is about 1 part by weight of total surfactant per 10 parts by weight of glyphosate acid equivalent.

Thus, in one embodiment, a herbicidal composition is provided as described hereinabove, further comprising at least one surfactant, wherein the weight ratio of glyphosate a.e. to total surfactant is not greater than about 10:1, for example about 2:1 to about 10:1. Illustratively the weight ratio of glyphosate a.e. to total surfactant is about 2.5:1 to about 8:1, for example about 3:1 to about 6:1.

The choice of surfactant or surfactants is not narrowly critical. One of ordinary skill in the art will be able to select a suitable surfactant or surfactant blend from among those known to enhance herbicidal effectiveness of glyphosate by routine experimentation based upon the information provided herein and in the literature pertaining to glyphosate formulations. See, for example, surfactants disclosed as components of glyphosate formulations in the patents and publications individually cited below, each incorporated herein by reference.

U.S. Pat. No. 6,455,473 to Wright.
International Patent Publication No. WO 99/21424.
International Patent Publication No. WO 01/89302.
Above-cited WO 03/013241.

The surfactant(s) can be present in solution (e.g., micellar solution) and/or in stable dispersion, for example as a suspension, emulsion or microemulsion, in the composition.

A surfactant that is a "major or sole surfactant component" herein constitutes about 50% to 100% by weight of all surfactants present in the composition. For the present purpose, the weight or concentration of a surfactant component as defined herein does not include non-amphiphilic compounds that are sometimes introduced with the surfactant component, such as water, isopropanol or other solvents, or glycols, such as ethylene glycol, propylene glycol or polyethylene glycols.

In one embodiment the composition comprises one or more surfactants each having a molecular structure comprising:
  (a) a hydrophobic moiety having one to a plurality of aliphatic, alicyclic or aromatic $C_{3-18}$ hydrocarbyl or hydrocarbylidene groups joined together by 0 to about 7 linkages selected from ether, thioether, sulfoxide, ester, thioester and amide linkages, the hydrophobic moiety having in total about 8 to about 24 carbon atoms; and
  (b) a hydrophilic moiety that comprises:
    (i) an amino group that is cationic or that can be protonated to become cationic, having attached directly thereto 0 to 3 oxyethylene groups or polyoxyethylene chains, such oxyethylene groups and polyoxyethylene chains comprising on average no more than about 15 oxyethylene units per surfactant molecule; and/or
    (ii) a glycoside or polyglycoside group comprising on average no more than about 2 glycoside units per surfactant molecule; the hydrophobic moiety being covalently attached (1) directly to an amino group of the hydrophilic moiety; (2) by an ether linkage incorporating an oxygen atom of an oxyethylene group or of a terminal oxyethylene unit of a polyoxyethylene chain of the hydrophilic moiety; or (3) by an ether linkage to a glycoside unit of the hydrophilic moiety.

According to the present embodiment, two subclasses of surfactant, defined by formulas (I) and (II) below, can be particularly useful.

A major or sole surfactant component can comprise one or more compounds having, at a pH of about 4, formula (I):

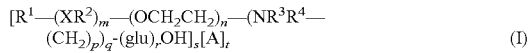

where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 8 such that the total number of carbon atoms in $R^1$—$XR^2)_m$ is about 8 to about 24, n is an average number of 0 to about 5, $R^3$ and $R^4$ are independently hydrogen or $C_{1-4}$ alkyl, p is 2 to 4, q is 0 or 1, glu is a unit of formula

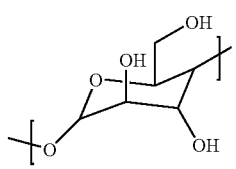

(referred to herein as a glucoside unit), r is an average number of about 1 to about 2, A is an anionic entity, and s is an integer of 1 to 3 and t is 0 or 1 such that electrical neutrality is maintained.

A major or sole surfactant component can comprise one or more compounds having, at a pH of about 4, formula (II):

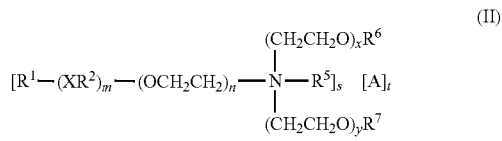

where $R^1$, X, $R^2$, m, n, A, s and t are as defined above for formula (I), $R^5$ is hydrogen, $C_{1-4}$ alkyl, benzyl, an anionic oxide group or an anionic group —$CH_2)_uC(O)O$ where u is 1 to 3, $R^6$ and $R^7$ are independently hydrogen, $C_{1-4}$ alkyl, $C_{2-4}$ acyl or $C_{1-4}$ carboxylic acid groups or $C_{1-4}$ alkyl esters of $C_{1-4}$ carboxylic acid groups, and x and y are average numbers such that x+y+n is not greater than about 15.

Surfactants conforming to formulas (I) and (II) above include without restriction those that are or can be described as alkyl polyglucosides, alkylaminoglucosides, polyoxyethylene alkylamines, polyoxyethylene alkyletheramines, alkyltrimethylammonium salts, alkyldimethylbenzylammonium salts, polyoxyethylene N-methyl alkylammonium salts, polyoxyethylene N-methyl alkyletherammonium salts, alkyldimethylamine oxides, polyoxyethylene alkylamine oxides, polyoxyethylene alkyletheramine oxides, alkylbetaines, alkylamidopropylamines and the like. The word or part-word "alkyl" as used in this paragraph reflects common usage in the art and means $C_{8-18}$ aliphatic, saturated or unsaturated, linear or branched hydrocarbyl.

When a maximum or minimum "average number" is recited herein with reference to a structural feature of a surfactant such as oxyethylene or glucoside units, it is to be understood that the integer number of such units in individual molecules in a surfactant preparation typically varies over a range that can include integer numbers greater than the maximum "average number" or smaller than a nonzero minimum "average number". The presence in a composition of individual surfactant molecules having an integer number of such units outside the stated range of "average number" does not remove the composition from the scope of the present embodiments, so long as the "average number" is within the stated range and other requirements are met.

Illustrative surfactant types that can be useful in compositions of the invention include those classified as types A to F below.

Type A: surfactants corresponding to formula (I) where $R^1$ is a $C_{8-18}$ aliphatic hydrocarbyl chain, m, n and q are 0, s is 1 and t is 0. This type includes several commercial surfactants collectively known in the art or referred to herein as alkyl polyglucosides or APGs. Suitable examples are sold by Cognis as Agrimul™ PG-2069 and Agrimul™ PG-2067.

Type B: surfactants corresponding to formula (II) where $R^1$ is a $C_{8-18}$ aliphatic hydrocarbyl chain and m is 0. In this type $R^1$ alone can be considered the hydrophobic moiety of the surfactant and is attached directly to the amino function, as in alkylamines, or by an ether linkage formed by the oxygen atom of an oxyethylene group or the terminal oxygen atom of a polyoxyethylene chain, as in certain alkyletheramines. Illustrative subtypes having different hydrophilic moieties include those classified as subtypes B1 to B5 below.

Subtype B1: x and y are 0, $R^5$ and $R^6$ are independently $C_{1-4}$ alkyl, $R^7$ is hydrogen and t is 1. This subtype includes (where $R^5$ and $R^6$ are methyl) several commercial surfactants collectively known in the art or referred to herein as alkyldimethylamines. Suitable examples are dodecyldimethylamine, available for example from Akzo-Nobel as Armeen™ DM12D, and cocodimethylamine and tallowdimethylamine, available for example from Ceca as Noram™ DMC D and Noram™ DMS D respectively. Such surfactants are generally provided in non-protonated form, the anion A not being supplied with the surfactant. However, in a glyphosate salt formulation at a pH of about 4-5, the surfactant will be protonated and it will be recognized that the anion A can be glyphosate, which is capable of forming dibasic salts.

Subtype B2: x and y are 0, $R^5$, $R^6$ and $R^7$ are independently $C_{1-4}$ alkyl and t is 1. This subtype includes (where $R^5$, $R^6$ and $R^7$ are methyl and A is a chloride ion) several commercial surfactants collectively known in the art or referred to herein as alkyltrimethylammonium chlorides. A suitable example is cocoalkyl trimethylammonium chloride, available for example from Akzo-Nobel as Arquad™ C.

Subtype B3: x and y are average numbers such that x+y is at least 2, $R^6$ and $R^7$ are hydrogen and t is 1. This subtype includes commercial surfactants collectively known in the art or referred to herein as polyoxyethylene alkylamines (where n is 0 and $R^5$ is hydrogen), certain polyoxyethylene alkyletheramines (where n is 1-5 and $R^5$ is hydrogen), polyoxyethylene N-methyl alkylammonium chlorides (where n is 0, $R^5$ is methyl and A is a chloride ion), and certain polyoxyethylene N-methyl alkyletherammonium chlorides (where n is 1-5, $R^5$ is methyl and A is a chloride ion). Suitable examples are polyoxyethylene (2) cocoamine, polyoxyethylene (5) tallowamine and polyoxyethylene (10) cocoamine, available for example from Akzo-Nobel as Ethomeen™ C/12, Ethomeen™ T/15 and Ethomeen™ C/20 respectively; a surfactant conforming, when its amine group is non-protonated, to formula (III):

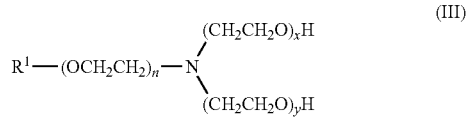

where $R^1$ is $C_{12-14}$ alkyl, n is 3 and x+y has an average value of about 5, as disclosed in U.S. Pat. No. 5,750,468 to Wright et al., incorporated herein by reference; and polyoxyethylene (2) N-methyl cocoammonium chloride and polyoxyethylene (2) N-methyl stearylammonium chloride, available for example from Akzo-Nobel as Ethoquad™ C/12 and Ethoquad™ 18/12 respectively. In cases where $R^5$ is hydrogen, i.e., in tertiary amine as opposed to quaternary ammonium surfactants, the anion A is typically not supplied with the surfactant. However, in a glyphosate salt formulation at a pH of about 4-5, the surfactant will be protonated and it will be recognized that the anion A can be glyphosate, which is capable of forming dibasic salts. In one sub-embodiment a sole or major surfactant component is a polyoxyethylene alkylamine surfactant wherein n is 0 and x+y is 2 to about 8, as disclosed in U.S. Pat. No. 5,668,085 to Forbes et al., incorporated herein by reference.

An illustrative surfactant useful in a composition of the invention is a polyoxyethylene fatty amine having about 7 to about 15 EO units, optionally in a blend with a polyoxyethylene fatty amine having about 2 to about 5 EO units. Such fatty amines can, without limitation, independently be selected from tallowamines, hydrogenated tallowamines, stearylamines, oleylamines, cetylamines, myristylamines, soyamines, cocoamines, laurylamines and mixtures thereof. For example, a high-EO tallowamine such as one having about 7.5, about 8, about 8.5, about 9, about 9.5, about 10, about 10.5, about 11, about 11.5, about 12, about 12.5, about 13, about 13.5, about 14, about 14.5 or about 15 EO units can optionally be blended with a low-EO cocoamine such as one having about 2, about 2.5, about 3, about 3.5, about 4, about 4.5 or about 5 EO units. Either or both of the tallowamine and the cocoamine components of such a blend can optionally be substituted, in whole or in part, with another fatty amine, for example a soyamine component. A suitable weight ratio of high-EO to low-EO fatty amine in such a blend can be, for example, about 50:50, about 55:45, about 60:40, about 65:35, about 70:30, about 75:25, about 80:20, about 85:15 or about 90:10.

In a variant of subtype B3, $R^6$ and $R^7$ are other than hydrogen. For example, the surfactant of formula (III) is a member of a class conforming to formula (IIIa):

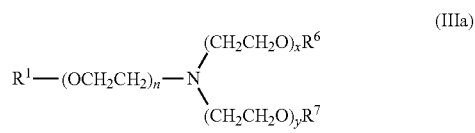

where $R^1$, n, x and y are as defined above, and $R^6$ and $R^7$ are independently selected from hydrogen, $C_{1-4}$ alkyl, $C_{2-4}$ acyl and $C_{1-4}$ carboxylic acid groups and $C_{1-4}$ alkyl esters of $C_{1-4}$ carboxylic acid groups. Illustratively $R^6$ and $R^7$ are the same and are selected from —H, —$CH_3$, —$C_2H_5$, —$CH(CH_3)_2$, —COOH, —$COOCH_3$, —$COOC_2H_5$, —$CH_2COOH$, —$CH_2COOCH_3$ and —$CH_2COOC_2H_5$ groups.

Subtype B4: $R^5$ is an anionic oxide group and t is 0. This subtype includes commercial surfactants collectively known in the art or referred to herein as alkyldimethylamine oxides (where n, x and y are 0, and $R^6$ and $R^7$ are methyl), alkyletherdimethylamine oxides (where n is 1-5, x and y are 0, and $R^6$ and $R^7$ are methyl), polyoxyethylene alkylamine oxides (where n is 0, x+y is at least 2, and $R^6$ and $R^7$ are hydrogen), and certain polyoxyethylene alkyletheramine oxides (where n is 1-5, x+y is at least 2, and $R^6$ and $R^7$ are hydrogen).

Suitable examples are cocodimethylamine oxide and polyoxyethylene (2) cocoamine oxide, available for example from Akzo-Nobel as Aromox™ DMC and Aromox™ C/12 respectively.

Subtype B5: $R^5$ is an acetate group, x and y are 0 and t is 0. This subtype includes commercial surfactants collectively known in the art or referred to herein as alkylbetaines (where n is 0 and $R^6$ and $R^7$ are methyl) and certain alkyletherbetaines (where n is 1-5 and $R^6$ and $R^7$ are methyl). A suitable example is cocobetaine, available for example from Cognis as Velvetex™ AB-45.

Type C: surfactants corresponding to formula (II) where $R^1$ is a $C_{8-18}$ aliphatic hydrocarbyl chain, m is 1, X is an ether linkage, $R^2$ is n-propylene and n is 0. In this type $R^1$ together with $OR^2$ can be considered the hydrophobic moiety of the surfactant which is attached directly by the $R^2$ linkage to the amino function. These surfactants are a subclass of alkyletheramines as disclosed in above-cited U.S. Pat. No. 5,750,468. Illustrative subtypes have the different hydrophilic moieties exemplified in subtypes B 1 to B5 above. Suitable examples are a surfactant conforming, when its amine group is non-protonated, to formula (IV):

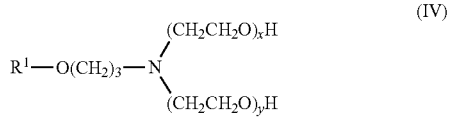

and a surfactant conforming to formula (V):

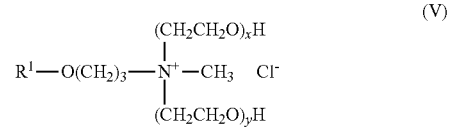

and a surfactant conforming to formula (VI):

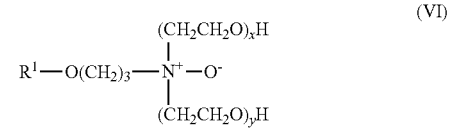

where, in each of formulas (IV), (V) and (VI), $R^1$ is $C_{10-13}$ alkyl (e.g., isodecyl, isotridecyl or cocoalkyl) and x+y has an average value of about 5, as disclosed in above-cited U.S. Pat. No. 5,750,468.

Type D: surfactants conforming to formula (II) where $R^1$ is a $C_{8-18}$ aliphatic hydrocarbyl chain, m is 1-5, each $XR^2$ is a group —OCH(CH$_3$)CH$_2$— and n is 0. In this type $R^1$ together with the —OCH(CH$_3$)CH$_2$— group(s) can be considered the hydrophobic moiety of the surfactant which is attached directly to the amino function. These surfactants are a further subclass of alkyletheramines as disclosed in above-cited U.S. Pat. No. 5,750,468. Illustrative subtypes have the different hydrophilic moieties exemplified in subtypes B1 to B5 above. A suitable example is a surfactant conforming, when its amine group is non-protonated, to formula (VII):

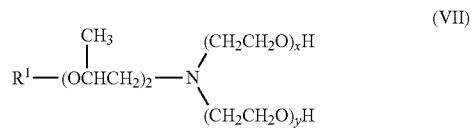

where $R^1$ is $C_{12-15}$ alkyl and x+y has an average value of about 5, as disclosed in above-cited U.S. Pat. No. 5,750,468.

The surfactant of formula (VII) is a member of a class conforming to formula (VIIa):

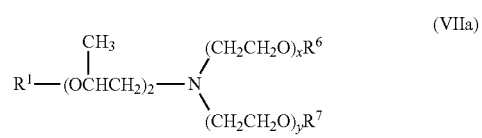

where $R^1$, x and y are as defined above, and $R^6$ and $R^7$ are independently selected from hydrogen, $C_{1-4}$ alkyl, $C_{2-4}$ acyl and $C_{1-4}$ carboxylic acid groups and $C_{1-4}$ alkyl esters of $C_{1-4}$ carboxylic acid groups. Illustratively $R^6$ and $R^7$ are the same and are selected from —H, —CH$_3$, —C$_2$H$_5$, —CH(CH$_3$)$_2$, —COOH, —COOCH$_3$, —COOC$_2$H$_5$, —CH$_2$COOH, —CH$_2$COOCH$_3$ and —CH$_2$COOC$_2$H$_5$ groups.

Another illustrative surfactant useful in a composition of the invention is an etheramine surfactant similar to that of formula (VII) but wherein x+y has an average value of about 7 to about 15, for example about 7.5, about 8, about 8.5, about 9, about 9.5 or about 10. An example of such a surfactant wherein x+y has an average value of about 8 is referred to herein as "etheramine 8EO". Such an etheramine can optionally be blended with a low-EO surfactant, for example a low-EO fatty amine surfactant such as a cocoamine having about 2, about 2.5, about 3, about 3.5, about 4, about 4.5 or about 5 EO units, at a weight ratio of about 40:60 to about 95:5, for example about 50:50, about 55:45, about 60:40, about 65:35, about 70:30, about 75:25, about 80:20, about 85:15 or about 90:10.

Type E: surfactants corresponding to formula (II) where $R^1$ is a $C_{8-18}$ aliphatic hydrocarbyl chain, m is 1, X is an amide linkage, $R^2$ is n-propylene and n is 0. In this type $R^1$ together with $XR^2$ can be considered the hydrophobic moiety of the surfactant which is attached directly by the $R^2$ linkage to the amino function. Commonly x and y are 0, $R^5$ is hydrogen or $C_{1-4}$ alkyl, $R^6$ and $R^7$ are independently $C_{1-4}$ alkyl and t is 1. A suitable example is cocoamidopropyl dimethylamine propionate, available for example from McIntyre as Mackalene™ 117.

Type F: surfactants corresponding to formula (II) where $R^1$ is hydrogen, m is 3-8 and each $XR^2$ is a group —OCH(CH$_3$)CH$_2$—. In this type the polyether chain of —OCH(CH$_3$)CH$_2$— groups (a polyoxypropylene chain) can be considered the hydrophobic moiety of the surfactant which is linked directly or via one or more oxyethylene units to the amino function. Commonly x and y are 0, $R^5$, $R^6$ and $R^7$ are independently $C_{1-4}$ alkyl and t is 1. Such surfactants are a subclass of polyoxypropylene quaternary ammonium surfactants as disclosed in U.S. Pat. No. 5,652,197 to Claude et al., incorporated herein by reference. In a suitable example, m is 7, n is 1, $R^5$, $R^6$ and $R^7$ are methyl and A is a chloride ion.

In surfactants of any of the above types where t is 1, A can be any suitable anion, for example chloride, bromide, iodide, sulfate, ethosulfate, phosphate, acetate, propionate, succinate, lactate, citrate, tartrate or, as indicated above, glyphosate.

In another embodiment a major or sole surfactant component comprises an N—($C_{8-18}$) acyl sarcosinate surfactant as disclosed in above-cited WO 99/21424. Suitable examples are N-lauroyl, N-cocoyl, N-oleoyl and N-stearoyl sarcosinates.

In another embodiment at least one surfactant is present in the composition, selected from the group consisting of polyoxyethylene fatty amines having 2 to about 12 moles of ethylene oxide per mole of fatty amine, alkyletheramines, quaternary ammonium surfactants, polyoxyethylene alkylphenols, alkyl polyglycosides, alkylbetaines, alkylamine oxides and mixtures thereof.

Compositions of the invention can optionally contain additional herbicidally inactive ingredients such as pH modulating agents (e.g., acidifying, basifying and/or buffering agents), defoaming agents, antidrift agents, coloring agents, and the like. Such additional ingredients should be selected so as not to require reduction of glyphosate a.e. concentration below about 360 g/l, nor significantly compromise physical stability at high glyphosate a.e. concentration, nor antagonize herbicidal activity of the composition to an unacceptable degree.

Compositions of the invention can optionally contain one or more additional herbicides (i.e., other than glyphosate). In practice, at the high glyphosate a.e. concentrations of the present compositions, the amount of a second herbicide that can be accommodated in a stable formulation is rather limited, but in certain situations a small amount of a herbicide such as glufosinate, an imidazolinone or a sulfonylurea can be useful.

Highly concentrated aqueous glyphosate potassium salt compositions exhibit relatively low viscosity and high density by comparison with glyphosate IPA salt compositions having equal glyphosate a.e. concentration. However, potassium glyphosate is much less compatible with a wide range of surfactants than IPA glyphosate, rendering the potassium salt less useful for preparing surfactant-containing formulations with high glyphosate loading. By admixture of a relatively small amount of IPA glyphosate with potassium glyphosate, a highly concentrated aqueous glyphosate formulation can be prepared having favorable viscosity and density properties, yet capable of containing an agronomically useful amount of any of a wide range of surfactants that are poorly compatible with potassium glyphosate alone.

An aqueous concentrate composition containing a mixture of potassium and IPA salts of glyphosate at a mole ratio of about 70:30 to about 90:10 and at a total glyphosate a.e. concentration illustratively of about 400 to about 600 g/l, with or without surfactant, can exhibit a lower freezing point than a comparative composition in which substantially all of the glyphosate is in the form of the potassium salt.

Furthermore, an aqueous concentrate composition containing a mixture of potassium and IPA salts of glyphosate at a mole ratio of about 70:30 to about 90:10 and at a total glyphosate a.e. concentration illustratively of about 400 to about 600 g/l, with or without surfactant, can exhibit a lower pour point than a comparative composition in which substantially all of the glyphosate is in the form of the potassium salt. By "pour point" is meant a temperature below which the composition is frozen or too viscous to be readily poured from a container.

Furthermore, an aqueous concentrate composition containing a mixture of potassium and IPA salts of glyphosate at a mole ratio of about 70:30 to about 90:10 and at a total glyphosate a.e. concentration illustratively of about 400 to about 600 g/l, with or without surfactant, can exhibit, at any selected temperature above the pour point, lower viscosity than a comparative IPA salt composition. This is a particularly great advantage where large volumes of the concentrate composition are to be transferred by gravity or by pumping, especially at low temperatures as can occur in early spring.

Mixed concentrated solutions of glyphosate potassium and IPA salts have been found to have lower viscosity than would be predicted from the viscosities of straight potassium salt and IPA salt solutions.

In various embodiments, a composition of the invention in absence of surfactant has a viscosity at 0° C. of not greater than about 300 cP, not greater than about 200 cP, not greater than about 150 cP, or not greater than about 100 cP. At glyphosate a.e. loadings lower than about 400 g/l, for example about 360 g/l, low temperature viscosity advantages of a mixed salt formulation as described herein over a straight IPA glyphosate composition are less pronounced than at higher loadings, but can still be sufficient to provide a useful benefit.

Furthermore, an aqueous concentrate composition containing a mixture of potassium and IPA salts of glyphosate at a mole ratio of about 70:30 to about 90:10 and at a total glyphosate a.e. concentration of about 400 to about 600 g/l, with or without surfactant, can exhibit higher density than a comparative IPA salt composition. Thus a given weight of glyphosate a.e. can be accommodated in a lesser volume than is required for the comparative composition. At glyphosate a.e. loadings lower than about 400 g/l, for example about 360 g/l, density advantages of a mixed salt formulation as described herein over a straight IPA glyphosate composition are less pronounced than at higher loadings, but can still be sufficient to provide a useful benefit.

Surfactant incompatibility with a concentrated glyphosate salt solution can be expressed in various ways, but generally results in a loss of physical stability, at low or more particularly at high temperatures. As glyphosate formulations are required to be stored in a wide range of temperature conditions, such loss of physical stability is highly undesirable.

A particularly useful measure of physical stability for surfactant-containing aqueous concentrate formulations of glyphosate salts is cloud point. Cloud point is a measure of the maximum or minimum temperature at which a specific such formulation forms a single-phase solution. At temperatures above a high temperature cloud point or below a low temperature cloud point, the surfactant separates from the solution, initially as a hazy or cloudy dispersion, and, upon standing, as a distinct phase generally rising to the surface of the solution. The term "cloud point" hereinbelow refers to a high temperature cloud point unless the context demands otherwise.

Cloud point of a composition can be determined by heating the composition until the solution becomes cloudy, and then allowing the composition to cool, with agitation, while its temperature is continuously monitored. A temperature reading taken when the solution clears is a measure of cloud point. What constitutes an acceptable cloud point is arbitrary, but for most purposes cloud point should be not lower than about 45° C., for example not lower than about 50° C., not lower than about 55° C., or not lower than about 60° C. Thus by one definition, a surfactant that is acceptably "compatible" in an aqueous concentrate glyphosate composition of the invention is one that, when present in a 360 g a.e./l composition at a glyphosate a.e./surfactant ratio of 10:1 by weight, exhibits a cloud point not lower than about 45° C. Other, more stringent, definitions of compatibility can be set forth by specifying a higher glyphosate a.e. concentration, for example 400 g a.e./l, a lower glyphosate a.e./surfactant ratio (i.e., a higher surfactant concentration for a given glyphosate a.e. concentration) and/or a higher cloud point.

A number of surfactants that are known to be incompatible with potassium glyphosate nonetheless exhibit acceptable cloud points in an aqueous concentrate composition containing a mixture of potassium and IPA salts of glyphosate at a mole ratio of about 70:30 to about 90:10 and at a total glyphosate a.e. concentration of about 400 to about 600 g/l, in some cases when the glyphosate a.e./surfactant ratio is as low as 4:1.

As noted above, compositions of the invention exhibit improved compatibility when tank-mixed with a phenoxy-type herbicide salt formulation, as evidenced at least by a reduced tendency to form a solid precipitate, or an increase in the time period needed for such a precipitate to form after preparation of the tank-mix.

"Improved compatibility" in the present context is by comparison with a glyphosate composition similar in all respects to the composition of the invention, except for the level of base excess. For example, a glyphosate potassium salt composition of the invention having about 10% to about 20% base excess exhibits improved compatibility with a phenoxy-type herbicide salt formulation by comparison with a comparative glyphosate potassium salt composition having about 5% base excess.

"Tank-mixing" herein embraces any method in agricultural use wherein a first herbicide composition and a second herbicide composition are diluted in water, in an amount suitable for application to a plant and/or soil surface by spraying, in any suitable vessel, most typically in a spray tank or in a pre-mixing tank. Order of addition of the water and the first and second herbicide compositions is not critical. Most commonly, however, the user first adds a portion of the water to the vessel, then adds the two herbicide compositions with agitation, then adds the remainder of the water, with continued agitation. Optionally other ingredients such as ammonium sulfate, additional surfactant, an anti-foam agent and/or a spray drift reduction additive can be added to a tank-mix.

A "phenoxy-type" herbicide herein is a salt-forming herbicide having a mode of action and/or selectivity towards broadleaved plant species that is characteristic of phenoxy herbicides or similar thereto. "Phenoxy herbicides" herein are salt-forming herbicides that include without limitation the following:

phenoxyacetic acids, for example:
4-chlorophenoxyacetic acid (4-CPA);
2,4-dichlorophenoxyacetic acid (2,4-D);
3,4-dichlorophenoxyacetic acid (3,4-DA);
4-chloro-2-methylphenoxyacetic acid (MCPA); and
2,4,5-trichlorophenoxyacetic acid (2,4,5-T);
phenoxypropanoic acids, for example:
2-(3-chlorophenoxy)propanoic acid (cloprop);
2-(4-chlorophenoxy)propanoic acid (4-CPP);
2-(2,4-dichlorophenoxy)propanoic acid (dichlorprop);
2-(3,4-dichlorophenoxy)propanoic acid (3,4-DP);
2-(2,4,5-trichlorophenoxy)propanoic acid (fenoprop); and
2-(4-chloro-2-methylphenoxy)propanoic acid (mecoprop); and
phenoxybutanoic acids, for example:
4-(4-chlorophenoxy)butanoic acid (4-CPB);
4-(2,4-dichlorophenoxy)butanoic acid (2,4-DB);
4-(3,4-dichlorophenoxy)butanoic acid (3,4-DB);
4-(4-chloro-2-methylphenoxy)butanoic acid (MCPB); and
4-(2,4,5-trichlorophenoxy)butanoic acid (2,4,5-TB);
including enantiomers (e.g., dichlorprop-P and mecoprop-P) as well as racemates thereof.

Salt-forming herbicides that are not phenoxy herbicides in a strict sense but fall within the above definition of "phenoxy-type" herbicides include without limitation the following:

benzoic acids, for example:
3-amino-2,5-dichlorobenzoic acid (chloramben);
3,6-dichloro-2-methoxybenzoic acid (dicamba);
2,3,6-trichlorobenzoic acid (2,3,6-TBA); and
2,3,5-trichloro-6-methoxybenzoic acid (tricamba);
picolinic acids, for example:
4-amino-3,6-dichloro-2-pyridinecarboxylic acid (aminopyralid);
3,6-dichloro-2-pyridinecarboxylic acid (clopyralid); and
4-amino-3,5,6-trichloro-2-pyridinecarboxylic acid (picloram); and
pyridinyloxyacetic acids, for example:
(3,5,6-trichloro-2-pyridinyl)oxyacetic acid (triclopyr);
including enantiomers as well as racemates thereof.

Among phenoxy-type herbicides, probably the most widely used in tank-mix with glyphosate is 2,4-D.

Phenoxy-type herbicides in the form of any agriculturally acceptable salt thereof, including potassium, sodium, ammonium and organic ammonium (more particularly low molecular weight organic ammonium) salts can be tank-mixed with a glyphosate potassium salt formulation of the invention. Low molecular weight organic ammonium salts include without limitation methylammonium, dimethylammonium (DMA), propylammonium (n-propylammonium and isopropylammonium), mono-, di- and triethanolammonium salts.

A phenoxy herbicide salt of particular interest is the DMA salt of 2,4-D.

Methods of use of glyphosate herbicidal formulations are well known in the art. An aqueous concentrate composition of the invention can be diluted in an appropriate volume of water to provide an application composition that can then be applied, for example by spraying, to foliage of plants such as weeds to be killed or controlled. For most purposes, an application composition, for example a spray-tank composition, is applied at a glyphosate a.e. rate of about 0.1 to about 5 kg/ha, occasionally more. Typical glyphosate a.e. rates for control of annual and perennial grasses and broadleaved plants are about 0.3 to about 1.5 kg/ha. A composition of the invention can be applied in any convenient volume of water, most typically about 50 to about 1,000 l/ha.

Likewise, methods of use of phenoxy-type herbicidal formulations are well known in the art. Suitable application rates vary depending on the particular phenoxy-type herbicide selected, the plant species to be killed or controlled, and other factors. In general, a suitable application rate is about 0.1 to about 5 kg/ha. Illustratively, typical a.e. rates for control of annual and perennial broadleaved plants are about 0.3 to about 2 kg/ha in the case of 2,4-D, about 0.2 to about 1 kg/ha in the case of dicamba, and about 0.02 to about 0.2 kg/ha in the case of picloram.

When tank-mixed with glyphosate, it is sometimes possible to reduce the rate of the phenoxy-type herbicide needed to achieve acceptable weed control. In general, suitable glyphosate/phenoxy-type herbicide a.e. ratios for tank-mixing are about 1:5 to about 20:1, depending again on the particular phenoxy-type herbicide selected, the plant species to be killed or controlled, and other factors. Illustratively, typical a.e. ratios are about 1:2 to about 5:1 in the case of 2,4-D, about 1:1 to about 10:1 in the case of dicamba, and about 2:1 to about 20:1 in the case of picloram.

A tank-mix herbicidal composition of the invention comprises, in an aqueous application medium, a glyphosate herbicide and a phenoxy-type herbicide, the composition being prepared by a process comprising admixing in a suitable vessel with agitation:

(i) water in an amount suitable for application to a plant and/or soil surface by spraying;

(ii) a herbicidally effective amount of a first aqueous concentrate herbicidal composition comprising in aqueous solution one to a plurality of salts of glyphosate at a total glyphosate a.e. concentration not less than about 360 g/l, wherein (a) the glyphosate is in anionic form accompanied by low molecular weight non-amphiphilic cations in a total molar amount of about 110% to about 120% of the molar amount of glyphosate; and (b) a major amount to substantially all of the low molecular weight non-amphiphilic cations are potassium cations; and (iii) a second aqueous concentrate herbicidal composition comprising in aqueous solution one to a plurality of salts of the phenoxy-type herbicide, in an amount providing a glyphosate to phenoxy-type herbicide a.e. ratio of about 1:5 to about 20:1.

Any glyphosate potassium salt composition (including those comprising a minor amount of a low molecular weight organic ammonium salt of glyphosate) as described hereinabove can be used as the first aqueous concentrate herbicidal composition according to the present embodiment. Any aqueous concentrate phenoxy-type herbicide salt formulation, including without limitation such formulations of any phenoxy-type herbicide as mentioned hereinabove, can be used as the second herbicidal composition according to the present embodiment. The first (glyphosate) herbicidal composition is included in a herbicidally effective amount, for example an amount providing, when applied at a selected spray volume, an application rate of about 0.1 to about 5 kg a.e./ha, for example about 0.3 to about 2.5 kg a.e./ha. The second (phenoxy-type) herbicidal composition is included in an amount providing a glyphosate to phenoxy-type herbicide a.e. ratio of about 1:5 to about 20:1, for example about 1:2 to about 5:1 where the phenoxy-type herbicide is 2,4-D, about 1:1 to about 10:1 where the phenoxy-type herbicide is dicamba, and about 2:1 to about 20:1 where the phenoxy-type herbicide is picloram.

The tank-mix composition comprises water as a spray vehicle, in an amount suitable for application to a plant and/or soil surface by spraying, more particularly in an amount suitable for delivery of the glyphosate and phenoxy-type herbicides to plants, for example weeds, that are to be killed or controlled.

Amounts of water are usually expressed in terms of "spray volume", i.e., the volume of spray solution (which is mostly water, making up the balance after accounting for the first and second herbicide compositions and other optional additives as described below) to be applied to a unit land area. Spray volume can be expressed in any suitable units such as liters/hectare (l/ha) or gallons/acre. Most commonly, spray volumes useful for tank-mix compositions of the present invention will be selected in a range of about 10 to about 1,000 l/ha, for example about 25 to about 500 l/ha.

Tank-mix compatibility challenges using state-of-the-art glyphosate compositions tend to be most severe at low spray volumes, where a spray solution having higher concentrations of both the glyphosate and the phenoxy-type herbicides is prepared. Thus, while tank-mix compositions of the present invention are useful at least across the wide range of spray volumes indicated above, these compositions bring especial benefit at low to moderate spray volumes, such as, for example, spray volumes of about 10 to about 200 l/ha, illustratively about 25 to about 100 l/ha, for example about 46.8 l/ha (5 U.S. gallons/acre) or about 93.5 l/ha (10 U.S. gallons/acre).

Tank-mix compatibility is also affected by aspects of water quality, especially water "hardness" resulting from presence of divalent and trivalent cations, mainly calcium ($Ca^{2+}$) and magnesium ($Mg^{2+}$) ions. Hardness is often expressed as parts per million (ppm or mg/l) calcium carbonate ($CaCO_3$), but typically includes all $Ca^{2+}$ and $Mg^{2+}$ ions, expressed as $CaCO_3$ equivalent concentration. Compatibility challenges tend to be greatest in hard water, for example water having hardness greater than about 75 ppm, more particularly where greater than about 150 ppm, especially where greater than about 300 ppm. Tank-mix compositions of the present invention can generally be prepared using water of hardness up to about 1,000 ppm or even higher.

Commonly, users of glyphosate herbicides, in particular where tank-mixes with a second herbicide are prepared, add an inorganic ammonium salt such as ammonium sulfate to the spray solution. Such addition is believed to have particular benefit in situations where water quality, including water hardness, is of concern. Accordingly, in one embodiment, a tank-mix composition as described above further comprises an inorganic ammonium salt, for example ammonium sulfate. Illustratively, ammonium sulfate can suitably be present in a tank-mix composition of the present embodiment at a concentration of about 5 to about 50 g/l, for example about 10 to about 20 g/l.

Other conventional additives to spray solutions, including additional surfactant(s), anti-foam agent(s), drift reduction additive(s), colorant(s), etc. can optionally be included in a tank-mix composition of the invention.

A process of the invention for preparing a tank-mix herbicidal composition comprises admixing in a suitable vessel with agitation:

(i) water in an amount suitable for application to a plant and/or soil surface by spraying;

(ii) a herbicidally effective amount of a first aqueous concentrate herbicidal composition comprising in aqueous solution one to a plurality of salts of glyphosate at a total glyphosate a.e. concentration not less than about 360 g/l, wherein (a) the glyphosate is in anionic form accompanied by low molecular weight non-amphiphilic cations in a total molar amount of about 110% to about 120% of the molar amount of glyphosate; and (b) a major amount to substantially all of the low molecular weight non-amphiphilic cations are potassium cations; and (iii) a second aqueous concentrate herbicidal composition comprising in aqueous solution one to a plurality of salts of the phenoxy-type herbicide, in an amount providing a glyphosate to phenoxy-type herbicide a.e. ratio of about 1:5 to about 20:1.

Order of addition is not narrowly critical, but it is generally good practice to add a portion, for example about one-fourth to about three-fourths, of the water to the vessel and commencing agitation before adding the first and second herbicide compositions. The remainder of the water can then be added to make up the desired spray volume. Where ammonium sulfate is to be used, it is generally best to add this before adding the herbicide compositions to ensure complete dissolution of the ammonium sulfate. Other additives such as a surfactant, an anti-foam agent and/or a drift reduction additive should also be added to the first portion of water before adding the herbicide compositions.

An illustrative procedure, using spray equipment having a spray tank having a filling port and a by-pass line, is as follows.

A 20 to 35 mesh screen is placed over the filling port. Through the screen, the spray tank is filled to about one-half the desired final volume with water, and agitation is started.

If ammonium sulfate is used, this is added slowly through the screen into the tank. Agitation is continued. No other materials are added until the ammonium sulfate is completely dissolved. A drift reduction additive, if desired, can now be added.

The first (glyphosate) and second (phenoxy-type) aqueous concentrate herbicide compositions are added, in either order or simultaneously, with continued agitation, optionally while adding the remainder of the water. The spray tank is filled with the remaining water to the desired final volume.

Good agitation should be maintained until and during spraying. The by-pass line should be kept near the bottom of the tank to minimize foaming. Screens in spray nozzles or in-line strainers should be no finer than 50 mesh.

Further information on preparation and application of tank-mixes can be found, for example, in the product label for Roundup WeatherMAX® herbicide of Monsanto Company, St Louis, Mo. (EPA Reg. No. 524-537), available for example at http://www.monsanto.com/monsanto/us_ag/content/crop_pro/roundup_weathermax/label.pdf and incorporated in its entirety herein by reference.

In a further embodiment of the invention, a method is provided for improving compatibility of an aqueous concentrate glyphosate potassium salt composition with an aqueous concentrate phenoxy-type herbicide salt composition when admixed with water to form a tank-mix composition, the method comprising adding a base in an amount sufficient to raise pH of the tank-mix composition to at least about 4.8.

According to this embodiment, the base can be added to the glyphosate composition, for example as described hereinbelow. Alternatively, the base can be added to the phenoxy-type herbicide salt composition. Alternatively, the base can be added during preparation of the tank-mix composition itself. Any combination of two or more of these three options for addition of base can be used.

Any convenient base can be used. For adding to the glyphosate composition, potassium hydroxide is an option but better results may be obtained with a low molecular weight organic amine such as monoethanolamine or especially isopropylamine. For adding to the phenoxy-type herbicide composition, a suitable option is to add a base supplying the same cationic species as used to prepare the herbicide salt; for example, in the case of the dimethylammonium salt of 2,4-D, additional dimethylamine can be added. For adding to the tank-mix composition in the field to prevent precipitation from occurring, suitable bases include without limitation sodium hydroxide, potassium hydroxide, aluminum hydroxide, ammonia, sodium bicarbonate, ammonium bicarbonate, etc.

There are practical limitations to the amount of base that can be added to either of the herbicide compositions. For example, adding enough base to the aqueous concentrate glyphosate potassium salt composition to provide a tank-mix composition pH above about 5 can compromise stability of the aqueous concentrate formulation, particularly where a surfactant is included in the formulation. However, no such limitation exists for adding a base to the tank-mix composition itself. Illustratively, a tank-mix composition pH of about 5 to about 7 can provide good results. A pH higher than about 7 can also be acceptable, but as pH increases there can be a tendency for the composition to release ammonia or a low molecular weight organic amine such as IPA or DMA, resulting in a strong odor and possible hazard. A base can be added at any stage during or after admixing of the other ingredients of the tank-mix composition.

It will be understood that the lower the pH of the tank-mix composition without added base, the more base should be added to ensure the pH is brought into a desirable range. Where ammonium sulfate is present in the tank-mix composition, for example to counteract effects of hard water, compatibility of a glyphosate potassium salt formulation and a 2,4-D dimethylammonium salt (or other phenoxy-type herbicide salt) formulation can be further compromised, especially at low spray volumes and/or relatively high 2,4-D rates. In such situations, a greater amount of base may be required.

Illustratively, tank-mix compatibility problems when a glyphosate potassium salt formulation such as Roundup® Original Max of Monsanto Company is mixed with a 2,4-D dimethylammonium salt formulation can be ameliorated by adding to the tank-mix composition a readily available base such as household ammonia (5% aqueous ammonia) or baking soda (sodium bicarbonate), in an amount sufficient to raise pH of the composition to about 5 or higher, for example about 5.2 or higher. Suitable pH targets are, for illustrative purposes only, about 5.5, about 5.7, about 5.9, about 6.1, about 6.3 or about 6.5. For example, where a spray volume of 46.8 l/ha (5 U.S. gallons/acre) is used, precipitation of solids can generally be substantially prevented by addition of household ammonia in an amount of about 4% by volume of the spray solution or by addition of baking soda in an amount of about 10 g/l. Lesser amounts of base, for example household ammonia at as little as 0.75% by volume of the spray solution, can be effective in many situations.

As compatibility problems tend to increase with increasing 2,4-D rate, a suitable amount of base for addition can be tied to the amount of the 2,4-D formulation to be included in the tank-mix composition. For example, household ammonia can illustratively be added in a volume/volume ratio to the 2,4-D formulation of about 0.5:1 to about 2.5:1, e.g., about 1:1 to about 1.25:1, with a ratio higher in the range being desirable at lower spray volumes. As a further example, baking soda can illustratively be added in an amount of about 100 to about 400 g, e.g., about 150 to about 250 g, per liter of the 2,4-D formulation. Ratios or amounts outside the ranges given above can also be useful in particular situations.

In situations where adequate measures have not been taken to prevent formation of a precipitate, tank-mixing aqueous concentrate glyphosate potassium salt and phenoxy-type herbicide compositions can, as indicated above, result in formation of a precipitate. In a still further embodiment of the invention, a method is provided for redissolving such a precipitate, the method comprising adding a base in an amount sufficient to redissolve the precipitate.

Suitable bases include without limitation those indicated above as useful for use in the field to prevent precipitation from occurring, e.g., sodium hydroxide, potassium hydroxide, ammonia, sodium bicarbonate, ammonium bicarbonate, etc. Upon appearance of a precipitate, the base should be added with sufficient agitation to redisperse any settled precipitate and prevent further settlement. Suitable amounts of base can be similar to those indicated above, but in some situations a greater amount of base may be needed to redissolve a precipitate than to prevent the precipitate from occurring in the first place.

As a yet further embodiment of the invention, a process is provided for preparing an aqueous concentrate glyphosate salt composition. The process comprises:
  (i) neutralizing glyphosate acid with potassium hydroxide and optionally a minor amount of a low molecular weight organic amine in presence of water to produce a slurry or concentrated glyphosate salt solution having a pH of about 4.4 to about 4.7;
  (ii) adding water if necessary and optionally at least one surfactant to produce a composition having a total glyphosate a.e. concentration not less than about 360 g/l; and (iii) adding a low molecular weight organic amine in an amount sufficient to provide a pH of about 4.8 to about 5.0 in the composition.

The low molecular weight organic amine can be added before, during or after addition of the water to produce the final composition.

Low molecular weight organic amines such as isopropylamine can be difficult or hazardous to handle, and, where it is desired to adjust pH as the final step in the process, it will often be found more convenient to add the organic amine when forming the glyphosate salt at an early stage of the process, and to use potassium hydroxide (KOH) for pH adjustment. In such a situation, the process comprises:

(i) neutralizing glyphosate acid with potassium hydroxide and a minor amount of a low molecular weight organic amine in presence of water to produce a slurry or concentrated glyphosate salt solution having a pH of about 4.4 to about 4.7;

(ii) adding water if necessary and optionally at least one surfactant to produce a composition having a total glyphosate a.e. concentration not less than about 360 g/l; and (iii) adding potassium hydroxide in an amount sufficient to provide a pH of about 4.8 to about 5.0 in the composition.

The low molecular weight organic amine used in the process can illustratively be methylamine, dimethylamine, propylamine (e.g., n-propylamine or isopropylamine), mono-, di- or triethanolamine. In one embodiment the low molecular weight organic amine is isopropylamine.

Where the composition to be prepared comprises a minor amount of a low molecular weight organic ammonium salt of glyphosate, the following nonlimiting process can be used.

In a first step, glyphosate acid is added to a glyphosate potassium salt solution having a glyphosate assay of at least about 40% a.e. by weight, to form a slurry. In a second step, isopropylamine, in an amount at least sufficient to neutralize the added glyphosate acid and to provide a base excess of about 10% to about 20% in the composition as a whole, is introduced to the slurry with mixing until all glyphosate is dissolved, to form a mixed glyphosate salt solution comprising potassium and IPA cations in the desired mole ratio. Neutralization of glyphosate acid is exothermic and it will generally be desirable to make provision for heat removal during the second step of this process.

The glyphosate acid can be added in substantially dry form or, conveniently, in a form of "wet cake", which can typically contain up to about 15% by weight of water.

If desired, another low molecular weight organic amine such as n-propylamine can be substituted for isopropylamine. Especially where very high glyphosate a.e. concentration (for example greater than about 540 g/l) is desired in the final product, it is desirable to use isopropylamine in anhydrous form, to avoid introducing more water than necessary.

Relative amounts of potassium salt, glyphosate acid and isopropylamine are selected to provide a mixed glyphosate salt solution having a base excess of about 10% to about 20% and a desired mole ratio of potassium to IPA cations, for example of about 55:45 to about 99:1, or about 60:40 to about 99:8. In one exemplary embodiment, the mole ratio is about 70:30 to about 90:10, for example about 75:25 to about 85:15, or about 77:23 to about 83:17, illustratively about 80:20. In another exemplary embodiment, the mole ratio is about 95:5 to about 99:1, for example about 96:4 to about 98:2, illustratively about 97:3.

In an optional further step of the process, water and optionally surfactant can be added to the mixed glyphosate salt solution to adjust glyphosate a.e. concentration of the mixed salt solution to a desired level not less than about 360 g/l, for example not less than about 400 g/l. If desired or necessary, further and final pH adjustment can be made at this stage to bring the pH into a range of about 4.8 to about 5. Suitably, such final pH adjustment can be made with potassium hydroxide.

One of skill in the art will be able to design a protocol to determine whether a glyphosate potassium salt test composition as provided herein exhibits improved tank-mix compatibility with a phenoxy-type herbicide salt composition. One illustrative protocol, for use where the phenoxy-type herbicide salt is a salt of 2,4-D and compatibility is to be tested at a low spray volume of 5 gallons/acre (47 l/ha) in presence of ammonium sulfate, is presented below.

Water of known hardness (e.g., 1,000 ppm) in an amount of 94.17 ml is added to a suitable vessel such as a 100 ml jar or beaker and agitated with a magnetic stir bar. Ammonium sulfate in an amount of 0.41 g is added. Once all the ammonium sulfate has dissolved, 3.33 ml of the glyphosate formulation and 2.5 ml of the 2,4-D formulation are added to bring the total volume of the resulting solution to 100 ml, and the time is noted.

Agitation is continued for the duration of the test (e.g., 12 hours) and the solution is examined at intervals. The time at which formation of a precipitate is first observed is recorded.

The volumes of the glyphosate and 2,4-D formulations given above correspond to a glyphosate formulation concentration of 540 g a.e./l applied at a rate of 1.33 pint/acre (1.56 l/ha), equivalent to 0.75 lb a.e./acre (0.84 kg a.e./ha); and a 2,4-D formulation applied at a rate of 1 pint/acre (1.17 l/ha). These volumes can be adjusted to simulate other application rates of glyphosate and 2,4-D, and the volume of water initially added can be adjusted accordingly.

Similarly, the amounts of the various ingredients added can readily be adjusted to simulate other spray volumes and other ammonium sulfate concentrations.

The invention is further illustrated but not limited by the following Examples.

EXAMPLES

Example 1

Tank mixtures of a commercial glyphosate potassium salt formulation (Roundup® Original Max of Monsanto Company) and a commercial 2,4-D dimethylammonium salt formulation (Agrisolution™ 2,4-D Amine of Agriliance LLC) were simulated by adding the following ingredients in the order shown to a 100 ml Nessler tube, with mixing by inversion:

1. 60 ml water, 342 ppm hardness;
2. 0-4 ml (see below) 5% aqueous ammonia;
3. 5.26 ml 2,4-D formulation;
4. water, 342 ppm hardness, q.s. for final volume of 100 ml;
5. 3.33 ml glyphosate formulation.

The volumes of ingredients were calculated to simulate a tank mixture for low spray volume (5 U.S. gallons/acre, or about 46.8 l/ha).

Without addition of aqueous ammonia, flocculation of solids occurred immediately and settled quickly. Solids could be resuspended by agitation, but would not dissolve.

In presence of up to 1 ml of 5% aqueous ammonia, no improvement in flocculation was observed. With increase in ammonia to 1.5 ml, flocculation was noticeably slower. In presence of 2-3.5 ml ammonia, flocculation took approximately 3-5 minutes to begin, and in presence of 4 ml ammonia, no flocculation occurred.

Example 2

Simulated tank mixtures were prepared as in Example 1, but with volumes of ingredients calculated to simulate 10 U.S. gallons/acre (about 93.5 l/ha), as follows:
1. 60 ml water, 342 ppm hardness;
2. 0-4 ml 5% aqueous ammonia;
3. 2.63 ml 2,4-D formulation;
4. water, 342 ppm hardness, q.s. for final volume of 100 ml;
5. 1.67 ml glyphosate formulation.

Without addition of aqueous ammonia, no flocculation of solids occurred immediately, but a precipitate appeared after about 1 hour. Precipitation was unaffected by addition of 0.5 ml of 5% aqueous ammonia, but in presence of 1 ml or more ammonia, no precipitation was observed.

Example 3

Tank mixtures of glyphosate potassium salt (Roundup® Original Max) and 2,4-D dimethylammonium salt (Agrisolution® 2,4-D Amine) were simulated by adding the following ingredients in the order shown to a 600 ml beaker, with mixing using a stir plate:
1. 366 ml water, 342 ppm hardness;
2. 20 ml 2,4-D formulation;
3. 13 ml glyphosate formulation.

Heavy precipitation was observed. After a 5 minute period to allow full development of the precipitate, 5% aqueous ammonia was added in 5 ml increments every 2 minutes.

Redissolution of the precipitate became evident by a degree of clearing of the solution after addition of 20 ml ammonia, but full redissolution required at least 25 ml ammonia. Even then, the solution remained slightly hazy.

Example 4

A precipitate formed by preparing a simulated tank mixture of glyphosate potassium salt (Roundup® Original Max) and 2,4-D dimethylammonium salt (Agrisolution™ 2,4-D Amine) was collected on filter paper. The resulting crystalline white solid was insoluble in acetone but soluble in water, providing a solution pH of 3.3. Analysis by NMR gave results that, together with the pH data, suggested that the precipitate was composed of about 70% 2,4-D potassium salt and about 30% 2,4-D acid. No more than traces of glyphosate or surfactant were evident.

Example 5

A simulated tank mixture was prepared in a Nessler tube with volumes of ingredients calculated to simulate 5 U.S. gallons/acre (about 46.8 l/ha), using the same glyphosate and 2,4-D formulations as above, with agitation as follows:
1. 91.67 ml water, 342 ppm hardness;
2. 0.5 g sodium bicarbonate;
3. 3.33 ml glyphosate formulation;
4. 5 ml 2,4-D formulation.

A clear solution was produced. No precipitation formed up to 30 minutes after preparation.

Example 6

A simulated tank mixture was prepared in a Nessler tube with volumes of ingredients calculated to simulate 5 U.S. gallons/acre (about 46.8 l/ha), using the same glyphosate and 2,4-D formulations as above, with agitation as follows:
1. 91.67 ml water, 342 ppm hardness;
2. 3.33 ml glyphosate formulation;
3. 5 ml 2,4-D formulation.

A precipitate formed within 30 seconds. Sodium bicarbonate was added in an amount of 0.5 g. Slight clearing of the solution was noted. With addition of a further 0.5 g sodium bicarbonate (total 1 g), the solution cleared quickly as the precipitate dissolved.

Example 7

Aqueous concentrate formulations (compositions 7-2 to 7-5) of glyphosate potassium salt were prepared at a glyphosate a.e. loading of 540 g/l, containing about 100 g/l of the surfactant of formula (VII) above and about 0.5 g/l of a silicone antifoam agent. An organic amine base, monoethanolamine (MEA), isopropylamine (IPA), triisopropylamine (TIPA) or dimethylethanolamine (DMEA) was added in an amount of 1% or 2% by weight to upwardly adjust pH of the formulation. A formulation without added base (composition 7-1) was prepared as a reference standard.

Cloud point of each pH-adjusted formulation was measured. A simulated tank-mix compatibility test was conducted for each formulation. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (Agrisolution™ 2,4-D Amine, Loveland™ 2,4-D Amine 4 or Saber™ herbicide of Loveland Products, Inc.) rate of 1 U.S. pint/acre (about 1.17 l/ha). Ingredients were added to a Nessler tube with agitation as follows:
1. 94.17 ml water, 1000 ppm hardness;
2. 3.33 ml glyphosate formulation;
3. 2.5 ml 2,4-D formulation.

Compatibility was measured by the length of time it took for a precipitate to begin forming in the tube. Results are shown in Table 1.

TABLE 1

Compatibility of glyphosate compositions with 2,4-D

| Composition | Base added | Cloud point | 2,4-D formulation | Time to form precipitate |
| --- | --- | --- | --- | --- |
| 7-1 | none | | Agrisolution | precipitate formed immediately |
| 7-2 | MEA 1% | 54° C. | | 5 min |
| 7-3 | MEA 2% | <45° C. | | 40 min |
| 7-4 | IPA 1% | 58° C. | | 10 min |
| 7-5 | IPA 2% | <50° C. | | >2 h (solution hazy) |
| 7-1 | none | | Loveland | 45 sec |
| 7-6 | TIPA 1% | 66° C. | | 2 min |
| 7-7 | TIPA 2% | 62° C. | | 2 min |
| 7-8 | DMEA 1% | 58° C. | | 15 min |
| 7-9 | DMEA 2% | <55° C. | | 60 min |
| 7-1 | none | | Saber | 20 min |
| 7-6 | TIPA 1% | 66° C. | | 90 min |
| 7-7 | TIPA 2% | 62° C. | | >2 h (solution cloudy) |
| 7-8 | DMEA 1% | 58° C. | | >2 h (solution cloudy) |
| 7-9 | DMEA 2% | <55° C. | | >2 h (solution cloudy) |

Example 8

Glyphosate potassium salt formulations having added IPA to improve compatibility with 2,4-D were further modified (compositions 8-1 to 8-5) by addition to or partial substitution of the surfactant of formula (VII) ("surfactant VII") with polyoxyethylene (2) cocoamine surfactant ("coco-2"), or by use of a surfactant system comprising polyoxyethylene (10.5) tallowamine ("tallow-10.5") and coco-2 (compositions 8-6 and 8-7), in an effort to increase cloud point, as detailed in Table 2.

TABLE 2

Modified potassium glyphosate formulations

| Composition | Ingredients[1] | Weight % | Loading (g/l) | Cloud point |
|---|---|---|---|---|
| 8-1 | glyphosate K salt[2] | 84.0 | 540 | 65° C. |
|  | surfactant VII | 7.5 | 102 |  |
|  | coco-2 | 2.5 | 34 |  |
|  | IPA | 1.0 |  |  |
| 8-2 | glyphosate K salt[2] | 84.0 | 540 | 62° C. |
|  | surfactant VII | 7.5 | 102 |  |
|  | coco-2 | 1.25 | 17 |  |
|  | IPA | 1.0 |  |  |
| 8-3 | glyphosate K salt[2] | 84.0 | 540 | 57° C. |
|  | surfactant VII | 6.0 | 82 |  |
|  | coco-2 | 1.5 | 20 |  |
|  | IPA | 2.0 |  |  |
| 8-4 | glyphosate K salt[2] | 84.0 | 540 | 55° C. |
|  | surfactant VII | 6.4 | 87 |  |
|  | coco-2 | 1.1 | 15 |  |
|  | IPA | 2.0 |  |  |
| 8-5 | glyphosate K salt[2] | 84.0 | 540 | 52° C. |
|  | surfactant VII | 6.8 | 92 |  |
|  | coco-2 | 0.8 | 10 |  |
|  | IPA | 2.0 |  |  |
| 8-6 | glyphosate K salt[3] | 83.0 | 540 | 54° C. |
|  | tallow-10.5 | 7.0 | 95 |  |
|  | coco-2 | 3.0 | 41 |  |
|  | IPA | 1.0 |  |  |
| 8-7 | glyphosate K salt[3] | 83.2 | 540 | 62° C. |
|  | tallow-10.5 | 6.0 | 81 |  |
|  | coco-2 | 2.6 | 35 |  |
|  | IPA | 1.0 |  |  |

[1]silicone antifoam agent (in most cases 0.05%) not shown; balance to 100% is water
[2]concentrated aqueous solution, glyphosate assay 47.2% a.e.
[3]concentrated aqueous solution, glyphosate assay 47.9% a.e.

A simulated tank-mix compatibility test similar to that of Example 7 was conducted for each of compositions 8-1 to 8-7, by comparison with composition 7-1 as a reference standard. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (UCPA™ 2,4-D Amine 4 or Agrisolution™ 2,4-D Amine) rate of 1 U.S. pint/acre (about 1.17 l/ha), together with ammonium sulfate, 4.1 g/l. Results are shown in Table 3.

TABLE 3

Compatibility of glyphosate compositions with 2,4-D

| Composition | 2,4-D formulation | Time to form precipitate |
|---|---|---|
| 7-1 | UCPA | 1 min |
| 8-1 |  | >40 min (solution clear) |
| 8-2 |  | 10 min |
| 8-3 |  | >40 min (solution clear) |
| 8-4 |  | >40 min (solution clear) |
| 8-5 |  | >40 min (solution clear) |
| 8-6 |  | >40 min (solution clear) |
| 8-7 |  | 20 min |
| 7-1 | Agrisolution | 1.3 min |
| 8-1 |  | 59.2 min |
| 8-2 |  | 11.6 min |
| 8-3 |  | 34.2 min |
| 8-4 |  | 56.2 min |
| 8-5 |  | 57.6 min |
| 8-6 |  | 73.3 min |
| 8-7 |  | 19.8 min |

Example 9

Glyphosate formulations (compositions 9-1 to 9-5) comprising a mixture of potassium and IPA salts at a 70/30 weight/weight ratio and various blends of tallow-10.5 and coco-2 were prepared, with addition of IPA to raise pH to 4.9 or higher, as detailed in Table 4. Cloud point and pH were determined for each formulation.

Measurement of pH was according to the following protocol. A 6.6 g sample of the formulation was weighed into a 150 ml beaker. Demineralized water was added to make a total solution mass of 100 g. The solution was agitated with a magnetic stirring bar. A pH meter capable of measuring pH to 2 decimal places, and fitted with an electrode with temperature compensation, was used for the measurement. The pH meter was calibrated with standard buffers at pH 4.0 and pH 7.0. The solution pH was recorded when a reading was obtained that was stable for at least 10 seconds. Between sample measurements, the electrode was washed with and stored temporarily in demineralized water. After all sample measurements, the calibration was rechecked against the pH 4.0 and pH 7.0 buffers. If significant drift was observed, the electrode was recalibrated, and pH of all samples measured again. After all measurements were complete, the electrode was washed thoroughly with demineralized water, and placed in a 1M KCl solution for long term storage.

TABLE 4

Modified glyphosate formulations

| Composition | Ingredients[1] | Weight % | Loading (g/l) | pH | Cloud point |
|---|---|---|---|---|---|
| 9-1 | glyphosate K/IPA salt[2] | 86.8 | 540 | 4.90 | 69° C. |
|  | tallow-10.5 | 7.3 | 96 |  |  |
|  | coco-2 | 1.8 | 24 |  |  |
|  | IPA | 1.0 |  |  |  |
| 9-2 | glyphosate K/IPA salt[2] | 86.8 | 540 | 4.99 | 62° C. |
|  | tallow-10.5 | 7.3 | 96 |  |  |
|  | coco-2 | 1.8 | 24 |  |  |
|  | IPA | 1.5 |  |  |  |
| 9-3 | glyphosate K/IPA salt[2] | 86.8 | 540 | 4.92 | 72° C. |
|  | tallow-10.5 | 6.8 | 90 |  |  |
|  | coco-2 | 2.3 | 30 |  |  |
|  | IPA | 1.0 |  |  |  |
| 9-4 | glyphosate K/IPA salt[2] | 86.8 | 540 | 4.96 | 66° C. |
|  | tallow-10.5 | 6.8 | 90 |  |  |
|  | coco-2 | 2.3 | 30 |  |  |
|  | IPA | 1.5 |  |  |  |
| 9-5 | glyphosate K/IPA salt[2] | 86.8 | 540 | 5.06 | 59° C. |
|  | tallow-10.5 | 6.8 | 90 |  |  |
|  | coco-2 | 2.3 | 30 |  |  |
|  | IPA | 2.0 |  |  |  |

[1]silicone antifoam agent (0.038%) not shown; balance to 100% is water
[2]concentrated aqueous solution, glyphosate assay 47.2% a.e.

A simulated tank-mix compatibility test similar to that of Example 7 was conducted for each of compositions 9-1 to 9-5, by comparison with Roundup® Original Max and Roundup® WeatherMAX® herbicides as reference standards. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (UCPA™ 2,4-D Amine 4) rate of 1 U.S. pint/acre (about 1.17 l/ha), together with ammonium sulfate, 4.1 g/l. Results are shown in Table 5.

TABLE 5

Compatibility of glyphosate compositions with 2,4-D

| Composition | Time to form precipitate |
|---|---|
| Roundup Original Max | 1 min |
| Roundup WeatherMAX | 10 min |
| 9-1 | >3 h, <24 h |
| 9-2 | >3 h, <24 h (precipitate very light) |
| 9-3 | >3 h, <24 h |
| 9-4 | >3 h, <24 h (precipitate very light) |
| 9-5 | >24 h (solution clear) |

Example 10

Glyphosate formulations (compositions 10-1 to 10-8), comprising potassium salt or potassium and IPA salts at a 70/30 weight/weight ratio, and various blends of tallowamine and coco-2 were prepared, with addition of IPA or 45% KOH to raise pH to 4.88 or higher, as detailed in Table 6. Cloud point and pH were determined for each formulation. The pH method was similar to that described in Example 9.

TABLE 6

Modified glyphosate formulations

| Composition | Ingredients[1] | Weight % | Loading (g/l) | pH | Cloud point |
|---|---|---|---|---|---|
| 10-1 | glyphosate K/IPA salt[2] | 86.6 | 540 | 4.89 | 69° C. |
|  | tallow-10.5 | 7.6 | 100 |  |  |
|  | coco-2 | 1.9 | 25 |  |  |
|  | IPA | 1.0 |  |  |  |
| 10-2 | glyphosate K/IPA salt[2] | 86.6 | 540 | 4.92 | 71° C. |
|  | tallow-10.5 | 7.4 | 98 |  |  |
|  | coco-2 | 2.5 | 33 |  |  |
|  | IPA | 1.0 |  |  |  |
| 10-3 | glyphosate K salt[3] | 84.0 | 540 | 4.93 | 65° C. |
|  | tallow-8 | 5.3 | 71 |  |  |
|  | coco-2 | 2.3 | 30 |  |  |
|  | IPA | 1.5 |  |  |  |
| 10-4 | glyphosate K salt[3] | 84.0 | 540 | 4.96 | 64° C. |
|  | tallow-8 | 5.5 | 75 |  |  |
|  | coco-2 | 3.0 | 40 |  |  |
|  | IPA | 1.5 |  |  |  |
| 10-5 | glyphosate K salt[3] | 84.0 | 540 | 4.94 | 70° C. |
|  | tallow-9 | 4.5 | 61 |  |  |
|  | coco-2 | 3.0 | 41 |  |  |
|  | IPA | 1.5 |  |  |  |
| 10-6 | glyphosate K salt[3] | 84.0 | 540 | 4.96 | 65° C. |
|  | tallow-9 | 5.1 | 69 |  |  |
|  | coco-2 | 3.4 | 46 |  |  |
|  | IPA | 1.5 |  |  |  |
| 10-7 | glyphosate K salt[3] | 84.0 | 540 | 4.88 | 63° C. |
|  | tallow-9 | 4.9 | 66 |  |  |
|  | coco-2 | 4.0 | 54 |  |  |
|  | 45% KOH | 2.0 |  |  |  |
| 10-8 | glyphosate K salt[3] | 83.7 | 540 | 4.90 | 63° C. |
|  | tallow-9 | 4.7 | 63 |  |  |
|  | coco-2 | 3.8 | 52 |  |  |
|  | 45% KOH | 2.25 |  |  |  |

[1]silicone antifoam agent (0.038%) not shown; balance to 100% is water
[2]concentrated aqueous solution, glyphosate assay 47.2% a.e.
[3]concentrated aqueous solution, glyphosate assay 47.5% a.e.

A simulated tank-mix compatibility test similar to that of Example 7 was conducted for compositions 10-1 to 10-8, by comparison with Roundup® Original Max herbicide as a reference standard. Also included as standards were aqueous concentrate compositions of glyphosate potassium salt and glyphosate IPA salt, with no surfactant or pH adjustment. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (UCPA™ 2,4-D Amine 4) rate of 1 U.S. pint/acre (about 1.17 l/ha), together with ammonium sulfate, 4.1 g/l. Results are shown in Table 7.

TABLE 7

Compatibility of glyphosate compositions with 2,4-D

| Composition | Time to form precipitate |
|---|---|
| Roundup Original Max | 2 min |
| glyphosate K salt | immediate |
| glyphosate IPA salt | >24 h (solution cloudy) |
| 10-1 | >9 h, <24 h |
| 10-2 | >9 h, <24 h (precipitate very light) |
| 10-3 | 4 h |
| 10-4 | >9 h, <24 h |
| 10-5 | 7 h |
| 10-6 | 4 h |
| 10-7 | 40 min |
| 10-8 | 1 h 20 min |

Example 11

Glyphosate potassium salt formulations (compositions 11-1 to 11-4) comprising various blends of tallow-9 and coco-2 were prepared, with addition of IPA to raise pH to 4.83 or higher, as detailed in Table 8. Cloud point and pH were determined for each formulation. The pH method was similar to that described in Example 9.

TABLE 8

Modified glyphosate potassium salt formulations

| Composition | Ingredients[1] | Weight % | Loading (g/l) | pH | Cloud point |
|---|---|---|---|---|---|
| 11-1 | glyphosate K salt[2] | 83.8 | 540 | 5.00 | 67° C. |
|  | tallow-9 | 5.1 | 69 |  |  |
|  | coco-2 | 4.2 | 56 |  |  |
|  | IPA | 1.5 |  |  |  |
| 11-2 | glyphosate K salt[2] | 83.8 | 540 | 4.99 | 64° C. |
|  | tallow-9 | 5.5 | 75 |  |  |
|  | coco-2 | 4.5 | 61 |  |  |
|  | IPA | 1.5 |  |  |  |
| 11-3 | glyphosate K salt[2] | 84.0 | 540 | 4.83 | 65° C. |
|  | tallow-9 | 5.3 | 72 |  |  |
|  | coco-2 | 3.6 | 48 |  |  |
|  | IPA | 1.25 |  |  |  |
| 11-4 | glyphosate K salt[2] | 84.0 | 540 | 4.91 | 63° C. |
|  | tallow-9 | 5.3 | 72 |  |  |
|  | coco-2 | 3.6 | 48 |  |  |
|  | IPA | 1.5 |  |  |  |

[1]silicone antifoam agent (0.038%) not shown; balance to 100% is water
[2]concentrated aqueous solution, glyphosate assay 47.5% a.e.

A simulated tank-mix compatibility test similar to that of Example 7 was conducted for each of compositions 11-1 to 11-4, by comparison with Roundup® Original Max herbicide as a reference standard. Also included were glyphosate mixed potassium/IPA salt compositions 9-2 and 9-4 from Example 9. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (UCPA™ 2,4-D Amine 4) rate of 1 U.S. pint/acre (about 1.17 l/ha), together with ammonium sulfate, 4.1 g/l. Results are shown in Table 9.

TABLE 9

Compatibility of glyphosate compositions with 2,4-D

| Composition | Time to form precipitate |
|---|---|
| Roundup Original Max | 40 sec |
| 9-2 | >9 h (solution cloudy), <24 h (precipitate light) |
| 9-4 | >9 h (solution cloudy), <24 h (precipitate light) |
| 11-1 | >9 h (solution clear), <24 h |
| 11-2 | >9 h (solution cloudy), <24 h (precipitate light) |
| 11-3 | 3.5 h |
| 11-4 | 4 h |

Example 12

Glyphosate potassium salt formulations (compositions 12-1 to 12-4) comprising a specific surfactant blend were prepared, with addition of KOH, monoethanolamine (MEA), triethanolamine (TEA) or ammonia to raise pH to 4.8 or higher, as detailed in Table 10. Cloud point and pH were determined for each formulation. The pH method was similar to that described in Example 9.

TABLE 10

Modified glyphosate potassium salt formulations

| Composition | Ingredients[1] | Weight % | Loading (g/l) | pH | Cloud point |
|---|---|---|---|---|---|
| 12-1 | glyphosate K salt[2] | 83.9 | 540 | 4.88 | 63° C. |
| | surfactant blend | 8.9 | 120 | | |
| | 45% KOH | 2.0 | | | |
| 12-2 | glyphosate K salt[2] | 84.0 | 540 | 4.96 | 60° C. |
| | surfactant blend | 8.9 | 120 | | |
| | 40% MEA | 2.0 | | | |
| 12-3 | glyphosate K salt[2] | 83.9 | 540 | 4.88 | 76° C. |
| | surfactant blend | 8.9 | 120 | | |
| | TEA | 2.47 | | | |
| 12-4 | glyphosate K salt[2] | 83.9 | 540 | 4.80 | 69° C. |
| | surfactant blend | 8.9 | 120 | | |
| | 30% aqueous ammonia | 2.0 | | | |

[1]silicone antifoam agent (0.038%) not shown; balance to 100% is water
[2]concentrated aqueous solution, glyphosate assay 47.5% a.e.

A simulated tank-mix compatibility test similar to that of Example 7 was conducted for each of compositions 12-1, 12-2 and 12-4, by comparison with Roundup® Original Max herbicide as a reference standard. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (Agrisolution™ 2,4-D Amine) rate of 1 U.S. pint/acre (about 1.17 l/ha), together with ammonium sulfate, 4.1 g/l. Results are shown in Table 11.

TABLE 11

Compatibility of glyphosate compositions with 2,4-D

| Composition | Time to form precipitate |
|---|---|
| Roundup Original Max | 30 sec |
| 12-1 | 2.5 h |
| 12-2 | >10 h, <20 h |
| 12-4 | >10 h, <20 h |

Example 13

A simulated tank-mix compatibility test similar to that of Example 7 was conducted for composition 12-3, by comparison with Roundup® Original Max herbicide as a reference standard. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (Agrisolution™ 2,4-D Amine) rate of 1 U.S. pint/acre (about 1.17 l/ha), together with ammonium sulfate, 4.1 g/l. Results are shown in Table 12.

TABLE 12

Compatibility of glyphosate compositions with 2,4-D

| Composition | Time to form precipitate |
|---|---|
| Roundup Original Max | 40 sec |
| 12-3 | 30 min |

Example 14

Glyphosate potassium salt compositions 10-6, 10-8 and 11-1, prepared as above, were compared with Roundup® Original Max herbicide in various simulated tank-mix compatibility tests similar to that of Example 7, wherein water temperature, water hardness and ammonium sulfate level were varied. Volumes of ingredients were calculated to simulate a spray volume of 5 U.S. gallons/acre (about 46.8 l/ha), a glyphosate a.e. rate of 0.75 lb/acre (about 0.84 kg/ha) and a 2,4-D formulation (Agrisolution™ 2,4-D Amine) rate of 1 U.S. pint/acre (about 1.17 l/ha). Results are shown in Table 13.

TABLE 13

Compatibility of glyphosate compositions with 2,4-D

| Temp. | Hardness (ppm) | $(NH_4)_2SO_4$ (g/l) | Composition | Time to form precipitate |
|---|---|---|---|---|
| ambient | 0 | 0 | Roundup Original Max | 1 h |
| | | | 10-8 | >24 h |
| | | | 10-6 | >24 h |
| | | | 11-1 | >24 h |
| ambient | 0 | 4.1 | Roundup Original Max | 4 min |
| | | | 10-8 | >10 h, <20 h |
| | | | 10-6 | >24 h |
| | | | 11-1 | >24 h |
| ambient | 342 | 0 | Roundup Original Max | 9 min |
| | | | 10-8 | >10 h, <24 h |
| | | | 10-6 | >24 h |
| | | | 11-1 | >24 h |
| ambient | 342 | 4.1 | Roundup Original Max | 5 min |
| | | | 10-8 | >24 h |
| | | | 10-6 | >24 h |
| | | | 11-1 | >24 h |

TABLE 13-continued

Compatibility of glyphosate compositions with 2,4-D

| Temp. | Hardness (ppm) | (NH$_4$)$_2$SO$_4$ (g/l) | Composition | Time to form precipitate |
|---|---|---|---|---|
| ambient | 1000 | 0 | Roundup Original Max | 5 min |
| | | | 10-8 | 6 h 35 min |
| | | | 10-6 | 6 h 20 min |
| | | | 11-1 | 3 h 38 min |
| ambient | 1000 | 5 | Roundup Original Max | 1.5 min |
| | | | 10-8 | 2 h |
| | | | 10-6 | 8-10 h |
| | | | 11-1 | 8-10 h |
| ambient | 1000 | 10 | Roundup Original Max | 40 sec |
| | | | 10-8 | 10 min |
| | | | 10-6 | 9-10 h |
| | | | 11-1 | 9-10 h |
| 10° C. | 1000 | 0 | Roundup Original Max | 1.5 min |
| | | | 10-8 | 11.5 min |
| | | | 10-6 | 21 min |
| | | | 11-1 | 17 min |
| 10° C. | 1000 | 4.1 | Roundup Original Max | 2 min |
| | | | 10-8 | 11 min |
| | | | 10-6 | 15 min |
| | | | 11-1 | 20 min |
| 4° C. | 1000 | 4.1 | Roundup Original Max | 3 min (heavy precipitate) |
| | | | 10-8 | 17 min (light precipitate) |
| | | | 10-6 | 16 min (light precipitate) |
| | | | 11-1 | 11 min (heavy precipitate) |

What is claimed is:

1. A herbicidal composition comprising an aqueous solution of a plurality of salts of glyphosate at a total glyphosate a.e. concentration not less than about 360 g/l, wherein (a) said glyphosate is in anionic form accompanied by low molecular weight non-amphiphilic cations in a total molar amount greater than 110% to a maximum of about 120% of the molar amount of said glyphosate; and (b) a major amount but less than 100% of the low molecular weight non-amphiphilic cations are potassium cations.

2. The composition of claim 1, having a total glyphosate a.e. concentration of about 360 to about 650 g/l.

3. The composition of claim 1, having a total glyphosate a.e. concentration of about 400 to about 600 g/l.

4. The composition of claim 1, wherein the balance to 100% of the low molecular weight non-amphiphilic cations is provided in part or in whole by low molecular weight organic ammonium cations.

5. The composition of claim 4, having a mole ratio of potassium to low molecular weight organic ammonium cations of about 55:45 to about 99:1.

6. The composition of claim 4, having a mole ratio of potassium to low molecular weight organic ammonium cations of about 70:30 to about 90:10.

7. The composition of claim 4, having a mole ratio of potassium to low molecular weight organic ammonium cations of about 96:4 to about 98:2.

8. The composition of claim 4, wherein said low molecular weight organic ammonium cations comprise isopropylammonium cations.

9. The composition of claim 1, having a measured pH of about 4.8 to about 5.

10. The composition of claim 1, comprising no more than a pH adjusting amount of low molecular weight organic ammonium cations.

11. The composition of claim 1, further comprising at least one surfactant.

12. The composition of claim 11, wherein the weight ratio of glyphosate a.e. to total surfactant is not greater than about 10:1.

13. The composition of claim 1, exhibiting improved tank-mix compatibility with a phenoxy-type herbicide salt formulation.

14. The composition of claim 13, wherein said improved compatibility is evidenced at least by a reduced tendency to form a solid precipitate or an increase in the time period needed for such a precipitate to form after preparation of the tank-mix.

15. The composition of claim 13, wherein the phenoxy-type herbicide is selected from the group consisting of phenoxyacetic acids, phenoxypropanoic acids, phenoxybutanoic acids, benzoic acids, picolinic acids and pyridinyloxyacetic acids.

16. The composition of claim 13, wherein the phenoxy-type herbicide is selected from the group consisting of 2,4-D, dicamba and picloram.

17. The composition of claim 13, wherein the phenoxy-type herbicide salt is a potassium, sodium, ammonium or organic ammonium salt.

18. The composition of claim 13, wherein the phenoxy-type herbicide salt is selected from the group consisting of methylammonium, dimethylammonium, n-propylammonium, isopropylammonium, mono-, di- and triethanolammonium salts.

19. The composition of claim 13, wherein the phenoxy-type herbicide salt is the dimethylammonium salt of 2,4-D.

20. The composition of claim 13, wherein said improved compatibility is exhibited at a glyphosate/phenoxy-type herbicide a.e. ratio of about 1:5 to about 20:1.

21. The composition of claim 1, wherein the total molar amount of said low molecular weight non-amphiphilic cations is about 112% to about 120% of the molar amount of said glyphosate.

* * * * *